United States Patent [19]

Yamamoto et al.

[11] 4,387,223
[45] Jun. 7, 1983

[54] PROCESS FOR PREPARING 2(1H)-QUINAZOLINONE DERIVATIVES

[75] Inventors: Michihiro Yamamoto, Nishinomiya; Shigenari Katayama, Takarazuka; Masao Koshiba, Nishinomiya; Hisao Yamamoto, Kobe, all of Japan

[73] Assignee: Sumitomo Chemical Company, Limited, Osaka, Japan

[21] Appl. No.: 748,145

[22] Filed: Dec. 6, 1976

[30] Foreign Application Priority Data

Dec. 11, 1975 [JP] Japan ................................. 50-148279

[51] Int. Cl.$^3$ .................. C07D 413/04; C07D 413/06; C07D 401/04; C07D 405/04
[52] U.S. Cl. .................................... 544/116; 544/119; 544/251; 544/284; 544/286
[58] Field of Search ................ 260/251 QB, 256.4 Q, 260/256.5 R, 247.1 L; 544/116, 119, 251, 284, 286

[56] References Cited

U.S. PATENT DOCUMENTS

| | | | |
|---|---|---|---|
| 3,509,149 | 4/1970 | Cusic et al. | 544/286 |
| 3,560,501 | 2/1971 | Walker | 544/292 |
| 3,686,174 | 8/1972 | Cooke et al. | 544/286 |
| 3,748,331 | 7/1973 | Cooke et al. | 544/251 |
| 3,937,705 | 2/1976 | Hardtmann | 544/286 |
| 4,048,168 | 9/1977 | Yamamoto et al. | 544/286 |
| 4,202,974 | 5/1980 | Yamamoto et al. | 544/286 |

FOREIGN PATENT DOCUMENTS

| | | |
|---|---|---|
| 93775 | 11/1972 | Fed. Rep. of Germany . |
| 2254325 | 7/1973 | Fed. Rep. of Germany . |
| 2012061 | 6/1969 | France . |
| 48-21955 | 7/1973 | Japan ................................. 544/286 |

OTHER PUBLICATIONS

Ritter, "J. Amer. Chem.Soc.", vol. 55, 1933, pp. 3322–3325.
Merck Index, Ninth Edition, p. 993.
Patai–"The Chemistry of the Carbon–Nitrogen Double Bond Interscience Publishers (1970)–p. 117.

*Primary Examiner*—Donald G. Daus
*Assistant Examiner*—James H. Turnipseed
*Attorney, Agent, or Firm*—Stevens, Davis, Miller & Mosher

[57] ABSTRACT

2(1H)-Quinazolinone and quinazolinethione derivatives having excellent pharmacological activities are produced in high yield with high purity by heating the corresponding 3,4-dihydro-2(1H)-quinazolinone or quinazolinethione derivatives together with sulfur in an inert solvent.

2 Claims, No Drawings

PROCESS FOR PREPARING 2(1H)-QUINAZOLINONE DERIVATIVES

This invention relates to a process for producing 2(1H)-quinazolinone derivatives.

More particularly, the present invention relates to a novel process for producing 2(1H)-quinazolinone and quianzolinethione derivatives of the formula,

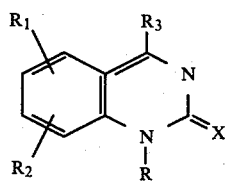

wherein $R_1$ and $R_2$ are each independently hydrogen, halogen, lower alkyl, lower alkoxyl, lower alkylthio, lower alkylsulfonyl, nitro, trifluoromethyl, lower alkanoyl,

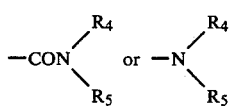

(in which $R_4$ and $R_5$ are each lower alkyl or, when taken together, $R_4$ and $R_5$ may form morpholino or piperidino together with the adjacent nitrogen atom), or when taken together, $R_1$ and $R_2$ may form methylenedioxy; $R_3$ is phenyl, halophenyl, nitrophenyl, lower alkylphenyl, lower alkoxyphenyl, pyridyl, furyl or thienyl; R is lower alkyl, lower alkenyl, lower cycloalkyl, lower cycloalkyl-lower alkyl, aralkyl, lower alkoxy-lower alkyl, lower haloalkyl, lower hydroxyalkyl or lower alkanoyloxy-lower alkyl; and X is oxygen or sulfur.

There has heretofore been known a process for producing the 2(1H)-quinazolinone derivatives by using a heavy metal oxide or salt thereof, for example, potassium permanganate, manganese dioxide or chromium trioxide as an oxidizing agent to introduce a double bond between the 3- and 4-positions of 3,4-dihydro-2(1H)-quinazolinone derivatives, as described in our Canadian Pat. No. 949,570. However, these reagents used in the prior process are relatively expensive and moreover in the case of adopting large scale manufacture, they may cause difficult problems of waste treatment and disposal from the standpoint of prevention of environmental pollution. Furthermore, according to the known process, it is very difficult to produce such compounds having sulfur as X in the formula (I).

The present inventors have extensively studied to improve the drawbacks of the known process, and have found that the process of the present invention can not only overcome such problems but also afford the desired compounds in high yield with high purity by a simple procedure.

Accordingly, the present invention provides a process for producing a 2(1H)-quinazolinone derivative of the formula (I) by heating a compound of the formula,

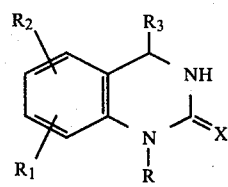

wherein $R_1$, $R_2$, $R_3$, R and X are as defined above, together with sulfur in an inert solvent.

The quinazolinone derivatives of the formula (I) which are obtained by the method of the present invention have excellent pharmacological activities such as anti-inflammatory, analgesic and anti-viral activities and they are very useful as synthetic medicinals.

In the compound of the formula (I), the term "alkyl" means a straight or branched alkyl, and the lower alkyl; includes, for example, $C_{1-4}$ alkyl such as methyl, ethyl, n-propyl, isopropyl, n-butyl and isobutyl; the lower alkoxyl includes; for example, $C_{1-4}$ alkoxyl such as methoxy, ethoxy, n-propoxy, isopropoxy, n-butoxy and isobutoxy; the lower alkenyl includes $C_{2-4}$ alkenyl, for example, allyl, and methallyl; the lower cycloalkyl includes, for example, $C_{3-8}$ cycloalkyl such as cyclopropyl, cyclobutyl, cyclopentyl, cyclohexyl, cycloheptyl and cyclooctyl; the aralkyl includes, for example, benzyl, halobenzyl and lower alkylbenzyl; the lower alkanoyl includes $C_{2-4}$ alkanoyl, for example, acetyl and propionyl; and lower hydroxyalkyl includes hydroxy-$C_{1-4}$ alkyl, for example, hydroxymethyl, 2-hydroxyethyl and 2-hydroxypropyl. The halogen referred to herein includes fluorine, chlorine, bromine and iodine, and the lower haloalkyl includes halo-$C_{1-4}$ alkyl, for example, 2-chloroethyl, 2,2-dichloroethyl, 2-fluoroethyl, 2,2-difluoroethyl, 2-chloro-2,2-difluoroethyl, 2,2,2-trifluoroethyl, 2-bromoethyl and 2,2,3,3,3-pentafluoropropyl.

In carrying out the process of the present invention, there is employed an inert solvent, which is selected from the group consisting of toluene, xylene, cymene, chlorobenzene, o-chlorotoluene, o-, m- or p-dichlorobenzene, tetrahydronaphthalene, decahydronaphthalene, pyridine, picoline, quinoline, dimethylformamide, dimethylacetamide, trichloroethane, tetrachloroethane and the like. In general, sulfur is preferably employed in excess, and the use of a few molar equivalents of sulfur per mole of the compound of the formula (II) is satisfactory. Reaction temperatures may vary depending upon the solvent and the starting material (II), and they are suitably in the range of about 100° to 200° C.

The present invention will be illustrated in more detail with reference to the following examples. However this is not intended to limit the scope of the invention.

EXAMPLE 1

A mixture of 1.62 g of 1-cyclopropylmethyl-4-phenyl-6-methoxy-3,4-dihydro-2(1H)-quinazolinethione, 0.48 g of sulfur and 10 ml of o-dichlorobenzene was stirred under reflux for 5 hours. The solvent was then removed under reduced pressure and the residue was chromatographed on a silica gel column, eluting with chloroform to give 1.26 g of 1-cyclopropylmethyl-4-phenyl-6-methoxy-2(1H)-quinazolinethione, m.p. 180°–181° C.

EXAMPLE 2

Using a procedure similar to that described in Example 1, the following 2(1H)-quinazolinethione derivatives were obtained in good yields.

1-Methyl-4-phenyl-6-chloro-2(1H)-quinazolinethione, m.p. 234°–235° C.
1-Ethyl-4-phenyl-2(1H)-quinazolinethione, m.p. 233°–234° C.
1-Isopropyl-4-phenyl-7-methyl-2(1H)-quinazolinethone, m.p. 195°–196° C.
1-Cyclopropylmethyl-4-phenyl-6-chloro-2(1H)-quinazolinethione, m.p. 231°–232° C.
1Cyclopropylmethyl-4-phenyl-7-methyl-2(1H)-quinazolinethione, m.p. 157°–158° C.
1-Cyclopropylmethyl-4-phenyl-2(1H)-quinazolinethione, m.p. 204°–205° C.
1-Cyclopropylmethyl-4-phenyl-6-methylthio-2(1H)-quinazolinethione, m.p. 174°–175° C.
1-Cyclopropylmethyl-4-phenyl-7-methoxy-2(1H)-quinazolinethione, m.p. 192°–193° C.
1-Cyclopropylmethyl-4-phenyl-6-nitro-2(1H)-quinazolinethione, m.p. 205°–206° C.
1-(2,2,2-Trifluoroethyl)-4-phenyl-6-chloro-2(1H)-quinazolinethione, m.p. 189°–190° C.
1-(2,2,2-Trifluoroethyl)-4-phenyl-6-methoxy-2(1H)-quinazolinethione, m.p. 194°–195° C.

EXAMPLE 3

A mixture of 1.54 g of 1-cyclopropylmethyl-4-phenyl-6-methoxy-3,4-dihydro-2(1H)-quinazolinone, 0.48 g of sulfur and 10 ml of o-dichlorobenzene was stirred under reflux for 5 hours. The solvent was then removed under reduced pressure, and the residue was treated with hot acetone. The insoluble sulfur was filtered off and the filtrate was concentrated to dryness. The residue was recrystallized from toluene to give 1.35 g of 1-cyclopropylmethyl-4-phenyl-6-methoxy-2(1H)-quinazolinone, m.p. 114°–115° C.

EXAMPLE 4

Using a procedure similar to that described in Example 3, the following compounds were obtained in good yields.
1-Cyclopropylmethyl-4-phenyl-2(1H)-quinazolinone, m.p. 154°–155° C.
1-Cyclopropylmethyl-4-phenyl-6-chloro-2(1H)-quinazolinone m.p. 174°–175° C.
1-Cyclopropylmethyl-4-phenyl-7-methyl-2(1H)-quinazolinone, m.p. 126°14 127° C.
1-Cyclopropylmethyl-4-phenyl-7-methoxy-2(1H)-quinazolinone, m.p. 169°–170° C.
1-Cyclopropylmethyl-4-phenyl-6-methylthio-2(1H)-quinazolinone, m.p. 133°–134° C.
1-Cyclopropylmethyl-4-phenyl-6-methylsulfonyl-2(1H)-quinazolinone, m.p. 186°–187° C.
1-Cyclopropylmethyl-4-phenyl-6-nitro-2(1H)-quinazolinone, m.p. 172°–173° C.
1-Cyclpropylmethyl-4-phenyl-6trifluoromethyl-2(1H)-quinazolinone, m.p. 166°–167° C.
1-Cyclopropylmethyl-4-phenyl-6-acetyl-2(1H)-quinazolinone, m.p. 194°–195° C.
1-Cyclopropylmethyl-4-phenyl-6,8-dichloro-2(1H)-quinazolinone, m.p. 158°–159° C.
1-Cyclopropylmethyl-4-phenyl-6,7-methylenedioxy-2(1H)-quinazolinone, m.p. 228°–229° C.
1-Cyclopropylmethyl-4-(o-fluorophenyl)-6-chloro-2(1H)-quinazolinone, m.p. 168°–169° C.
1-Cyclopropylmethyl-4-(p-nitrophenyl)-6-methoxy-2(1H)-quinazolinone, m.p. 147°–149° C.
1-Cyclopropylmethyl-4-(o-tolyl)-6-chloro-2(1H)-quinazolinone, m.p. 204°–205° C.
1-Cyclopropylmethyl-4-(p-methoxyphenyl)-6-methoxy-2(1H)-quinazolinone, m.p. 151°–152° C.
1-Cyclohexylmethyl-4-phenyl-6-nitro-2(1H)-quinazolinone, m.p. 201°–202° C.
1-Cyclohexyl-4-phenyl-6-nitro-2(1H)-quinazolinone, m.p. 186°–187° C.
1-Cyclopropylmethyl-4-(2-pyridyl)-6-chloro-2(1H)-quinazolinone, m.p. 120°–121° C.
1-Cyclopropylmethyl-4-(2-thienyl)-6-methoxy-2(1H)-quinazolinone, m.p. 145°–146° C.
1-Cyclopropylmethyl-4-(2-furyl)-6-chloro-2(1H)-quinazolinone, m.p. 160°–161° C.
1-Ethyl-4-phenyl-6-chloro-2(1H)-quinazolinone, m.p. 167°–168° C.
1-Isopropyl-4-phenyl-6-methoxy-2(1H)-quinazolinone, m.p. 140°–142° C.
1-Isopropyl-4-phenyl-7-methoxy-2(1H)-quinazolinone, m.p. 134°–136° C.
1-Isopropyl-4-phenyl-7-methyl-2(1H)-quinazolinone, m.p. 141°–142° C.
1Isopropyl-4-phenyl-6-dimethylamino-2(1H)-quinazolinone, m.p. 167°–168° C.
1-Allyl-4-phenyl-6-nitro-2(1H)-quinazolinone, m.p. 201°–202° C.
1-Benzyl-4-phenyl-6-nitro-2(1H)-quinazolinone, m.p. 173°–174° C.
1-(o-Methylbenzyl)-4-phenyl-6-nitro-2(1H)-quinazolinone, m.p. 200°–201° C. 1-Methoxymethyl-4-phenyl-6-chloro-2(1H)-quinazolinone, m.p. 165°–166° C.
1-(2-Ethoxyethyl)-4-(o-fluorophenyl)-6-chloro-2(1H)-quinazolinone, m.p. 146°–147° C.
1-(2-Ethoxyethyl)-4-phenyl-6-nitro-2(1H)-quinazolinone, m.p. 128°–129° C.
1-(2-Chloroethyl)-4-phenyl-6-nitro-2(1H)-quinazolinone, m.p. 190°–191° C.
1-(2-Chloro-2,2-difluoroethyl)-4-phenyl-6-methoxy-2-(1H)-quinazolinone, m.p. 155°–156° C.
1-(2,2,2-Trifluoroethyl)-4-phenyl-2(1H)-quinazolinone, m.p. 181°–182° C.
1-(2,2,2-Trifluoroethyl)-4-phenyl-6-chloro-2(1H)-quinazolinone, m.p. 185°–186° C.
1-(2,2,2-Trifluoroethyl)-4-phenyl-6-methoxy-2(1H)-quinazolinone, m.p. 157°–158° C.
1-(2,2,2-Trifluoroethyl)-4-phenyl-6-nitro-2(1H)-quinazolinone, m.p. 207°–208° C.
1-(2,2,2-Trifluoroethyl)-4-phenyl-6-methyl-2(1H)-quinazolinone, m.p. 178°–179° C.
1-(2,2,2-Trifluoroethyl)-4-phenyl-6,7-methylmedioxy-2(1H)-quinazolinone, m.p. 236°–237° C.
1-(2,2,3,3,3-Pentafluoropropyl)-4-phenyl-6-methoxy-2(1H)-quinazolinone, m.p. 135°–136° C.
1-(2,2,2-Trifluoroethyl)-4-(2-thienyl)-6-methoxy-2(1H)-quinazolinone, m.p. 157°–158° C.
1-(2-Hydroxyethyl)-4-phenyl-6-nitro-2(1H)-quinazolinone, m.p. 224°–225° C.
1-(2-Acetoxyethyl)-4-phenyl-6-methoxy-2(1H)-quinazolinone, m.p. 193°–194° C.

What is claimed is:
1. A process for producing a 2(1H)-quinazolinone derivative of the formula,

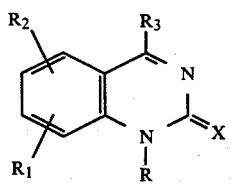

wherein $R_1$ and $R_2$ are each independently hydrogen, halogen, lower alkyl, lower alkoxyl, lower alkylthio, lower alkylsulfonyl, nitro, trifluoromethyl, lower alkanoyl,

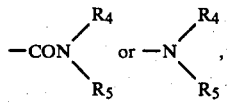

in which $R_4$ and $R_5$ are each lower alkyl or, when taken together, $R_4$ and $R_5$ may from morpholino or piperidino together with the adjacent nitrogen atom, or when taken together, $R_1$ and $R_2$ may form methylene dioxy; $R_3$ is phenyl, mono-halophenyl, mono-nitrophenyl, mono lower alkylphenyl, mono lower alkoxyphenyl, pyridyl, furyl or thienyl; R is lower alkyl, lower alkenyl, lower cycloalkyl, lower cycloalkyl-lower alkyl, benzyl, halobenzyl, lower alkyl benzyl, lower alkoxy-lower alkyl, lower haloalkyl, lower hydroxyalkyl or lower alkanoyloxy-lower alkyl; and X is sulfur, which comprises heating a compound of the formula,

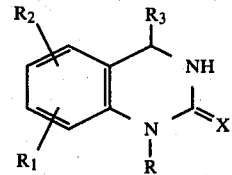

wherein $R_1$, $R_2$, $R_3$, R and X are as defined above, together with a molar excess of sulfur in an inert solvent at a temperature in the range of about 100° to 200° C.

2. A process according to claim 1, wherein the solvent is toluene, xylene, cymene, chlorobenzene, o-chlorotoluene, o-, m- or p-dichlorobenzene, tetrahydronaphthalene, decahydronaphthalene, pyridine, picoline, quinoline, dimethylformamide, dimethylacetamide, trichloroethane or tetrachloroethane.

* * * * *